United States Patent
Oota et al.

(10) Patent No.: US 6,914,169 B1
(45) Date of Patent: Jul. 5, 2005

(54) PATCH AGENT

(75) Inventors: Shigeo Oota, Tokyo (JP); Kiyomi Tsuruda, Tosu (JP)

(73) Assignee: Hisamitsu Pharmaceutical., Inc., Saga (JP)

(*) Notice: Subject to any disclaimer, the term of this patent is extended or adjusted under 35 U.S.C. 154(b) by 0 days.

(21) Appl. No.: 10/276,423

(22) PCT Filed: May 19, 2000

(86) PCT No.: PCT/JP01/03806

§ 371 (c)(1),
(2), (4) Date: Nov. 15, 2002

(87) PCT Pub. No.: WO01/87275

PCT Pub. Date: Nov. 22, 2001

(30) Foreign Application Priority Data

May 19, 2000 (JP) .................................. 2000-148260

(51) Int. Cl.[7] .............................................. A61F 13/00
(52) U.S. Cl. ................................ 602/58; 43/54; 43/57
(58) Field of Search ............ 602/41–59; 424/443–449; 128/888, 889

(56) References Cited

U.S. PATENT DOCUMENTS 3,665,918 A * 5/1972 Lindquist et al. ............. 602/75
3,990,603 A * 11/1976 Brochman .................. 220/260
4,510,197 A * 4/1985 Shah .......................... 428/220
5,378,536 A * 1/1995 Miller et al. ........... 428/355 RA

FOREIGN PATENT DOCUMENTS

| EP | 0 976 405 A1 | 2/2000 | |
|---|---|---|---|
| EP | 1 034 781 A2 | 9/2000 | |
| JP | 8-165251 | 6/1996 | |
| JP | 10-265372 | 10/1998 | |
| JP | 11-35453 | 2/1999 | |
| WO | WO 98/46267 | 10/1998 | |
| WO | 0026293 | * 5/2000 | ........... C08L/15/00 |

* cited by examiner

*Primary Examiner*—Kim M. Lewis
(74) *Attorney, Agent, or Firm*—Fitch, Even, Tabin & Flannery

(57) ABSTRACT

The patch agent of the present invention is a patch agent comprising a support made of a synthetic fiber and an adhesive layer mounted on the support, and having a bending resistance of 10 to 30 mm and a probe tack value of 0.25 to 1.2 N. The patch agent of the present invention can fully be prevented from peeling off at the time of application and can fully suppress the rash of skin and the pain upon peeling.

3 Claims, 2 Drawing Sheets

PATCH AGENT

CROSS-REFERENCED APPLICATIONS

This application is a National phase of International Application PCT/JP01/03806, filed May 2, 2001, which designated the U.S. and that International Application was not published under PCT Article 21(2) in English.

TECHNICAL FIELD

The present invention relates to a patch agent; and, more specifically, to a patch agent which can fully be prevented from peeling off when employed in a plaster agent or poultice agent, whereas the rash of skin and the pain upon peeling are suppressed.

BACKGROUND ART

A number of medical patch agents, such as transdermal absorbent and adhesive plaster tape, in which an adhesive layer containing a medicine is mounted on a support have conventionally been made. While such patch agents are required to have such characteristics that they do not peel off even when applied to parts such as joints and faces where movements are large and skins expand and constrict drastically, and neither rash nor flare occurs in the skin even when applied thereto for a long period of time. In the conventional patch agents, those hard to peel off have been likely to generate a rash or flare in the skin and accompany a pain upon peeling off, whereas those less irritative to skins have been easy to peel off.

Therefore, research and development have been under way from the viewpoint of the elasticity of support, the adhesiveness of adhesive layer, and the like in order to satisfy both high peeling prevention (resistance to peel) and low skin irritation (suppression of rashes in the skin and pains upon peeling), and various patch agents have been proposed. For example, Japanese Patent Application Laid-Open No. HEI 9-255563 discloses a technique in which the ratio in length between the longer and shorter sides in a rectangular patch agent and the bending resistance in the longitudinal direction are controlled so as to yield a skin traceability. Also, Japanese Patent Application Laid-Open No. HEI 10-226638 discloses a technique in which a support having a low bending resistance is provided with an adhesive planar substance, so as to provide the support with a softness. Further, Japanese Patent Application Laid-Open No. HEI 11-35453 discloses a patch agent whose adhesive layer contains oleic acid alkyl ester, so as to reduce the peeling force.

Even in the above-mentioned patch agents, however, if the adhesiveness of adhesive layer is fully lowered in order to prevent rashes from occurring, then the skin adhesion becomes insufficient, so that they are easier to peel off. If a sufficient adhesiveness is provided thereto so that they do not peel off even when applied to a part whose movement is large, then the skin is likely to suffer a rash, whereas pains accompany the peeling, where by a vicious circle occurs.

Thus, the conventional patch agents have not yet been sufficient for satisfying opposite characteristics of high peeling prevention (resistance to peel) and low skin irritation (suppression of rashes in the skin and pains upon peeling) with a favorable balance.

DISCLOSURE OF THE INVENTION

In view of the problems in the above-mentioned prior art, it is an object of the present invention to provide a patch agent which is fully prevented from peeling off at the time of application and fully suppresses rashes in the skin and pains upon peeling.

The inventors repeatedly carried out diligent studies in order to achieve the above-mentioned object and, as a result, have found that, if physical properties are taken into consideration independently for the support and adhesive layer when studying the peeling prevention and skin irritation as in the prior art, then it is difficult to satisfy these opposite characteristics at the same time; and that, when the bending resistance and probe tack value of a patch agent itself constructed and integrated by the support and adhesive layer satisfies predetermined conditions, it yields a patch agent which is fully prevented from peeling off when applied to parts such as joints and faces where movements are large and skins expand and constrict drastically, and the rash of skin and the pain upon peeling are fully suppressed; whereby the present invention has been accomplished.

Namely, the patch agent of the present invention is a patch agent comprising a support made of a synthetic fiber and an adhesive layer mounted on the support, said patch agent having a bending resistance of 10 to 30 mm and a probe tack value of 0.25 to 1.2 N.

According to the present invention, since the bending resistance of patch agent is 10 to 30 mm, and its probe tack value is 0.25 to 1.2 N, the skin traceability at the time of application is enhanced while the skin irritation is fully lowered, whereby it is fully prevented from peeling off while rashes of skin and pains upon peeling are fully suppressed.

The bending resistance refers to a value measured under the following conditions by the 45° cantilever method defined by JIS L 1085. Namely, the bending resistance in accordance with the present invention refers to the distance [mm] by which a test piece of 2 cm (shorter side)×about 15 cm (longer side) arranged on a horizontal table with smooth surfaces having a slanted face of 45° at one end and a scale on the upper face such that the shorter side of the test piece and the baseline of the scale coincide with each other is mildly slid in the direction of the slanted face until the center point of one of the shorter sides of the test piece abuts against the slanted face. Though the patch agent of the present invention may comprise a release sheet attached to the surface of adhesive layer as will be explained later, the bending resistance of patch agent in the present invention refers to the bending resistance of the patch agent including no release sheet, i.e., the bending resistance of the patch agent itself in which the support and the adhesive layer are integrated with each other.

The probe tack value in accordance with the present invention refers to the value measured under the following conditions in conformity to the method defined in ASTM D 2979. Namely, by using the probe tack tester defined in ASTM D 2979, after one bottom face of a cylinder (probe) made of Bakelite having a diameter of 5 mm and an adhesive layer surface of a test piece having a predetermined area are brought into contact with each other at a contact load of 0.98±0.001 N/cm$^2$ for a contact time of 1.0±0.01 seconds, the probe is separated from the adhesive layer surface in the perpendicular direction of the latter at a separating speed of 5±0.1 mm/s. The probe tack value in accordance with the present invention refers to the force [N] required at the time of separation.

As mentioned above, the patch agent of the present invention may comprise a release sheet attached to the surface of the adhesive layer, and the release sheet preferably has a bending resistance of 60 to 160 mm.

Preferably, the support used in the patch agent of the present invention is made of a polyester fiber having a fiber size (a fiber fineness) of 30 to 75 deniers, and has a weight per area of 80 to 120 g/m$^2$.

BEST MODES FOR CARRYING OUT THE INVENTION

Figure 1:
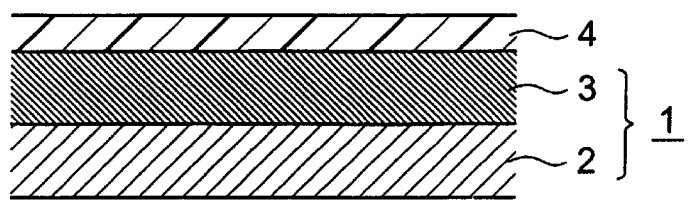
FIG. 1 is a schematic sectional view showing a preferred embodiment of the patch agent of the present invention.

In the following, preferred embodiments of the present invention will be explained in detail with reference to the drawings when necessary. In the drawings, parts identical or equivalent to each other will be referred to with numerals identical to each other.

FIG. 1 is a schematic sectional view showing a preferred embodiment of the patch agent of the present invention. In FIG. 1, a patch agent 1 comprises a support 2 and an adhesive layer 3 mounted on a surface thereof, whereas a release sheet 4, which is peeled off at the time of use, is preferably attached to a surface of the adhesive layer 3. In thus configured patch agent 1 of the present invention, the above-mentioned bending resistance is 10 to 30 mm, and the above-mentioned probe tack value is 0.25 to 1.2 N. Since the patch agent 1 itself has a bending resistance of 10 to 30 mm and a probe tack value of 0.25 to 1.2 N, it satisfies a sufficiently high peeling prevention (resistance to peel) and a sufficiently low skin irritation (suppression of rashes in the skin and pains upon peeling), which are characteristics usually opposing each other, at the same time.

Namely, if the above-mentioned two conditions are satisfied at the same time, both of the support and adhesive layer constituting the patch agent can fully trace the skin, even without increasing the adhesiveness of patch agent, when applied to joints such as elbows and knees where movements are large and faces and the like where very minute movements occur continuously, whereby the skin irritation can be reduced while keeping a sufficiently high peeling prevention.

The bending resistance of the patch agent of the present invention itself is 10 to 30 mm as mentioned above, preferably 10 to 25 mm. As the bending resistance of the patch agent is lower, its skin traceability tends to improve, whereby it is prevented from peeling off. However, if the bending resistance is less than the lower limit mentioned above, then the supportiveness becomes insufficient, so that the patch agent may get entangled or wrinkled at the time of application, whereby it becomes harder to handle. If the bending resistance of patch agent exceeds the upper limit mentioned above, by contrast, the skin traceability becomes insufficient, so that it is likely to peel off even upon a little movement.

The probe tack value of the patch agent of the present invention itself is 0.25 to 1.2 N as mentioned above, preferably 0.3 to 1.0 N. If the probe tack value of patch agent is less than the lower limit mentioned above, then the skin adhesiveness of patch agent becomes insufficient, so that it is likely to peel off even upon a little movement. If the probe tack value of patch agent exceeds the upper limit mentioned above, on the other hand, the skin irritation increases so much that rashes in the skin and pains upon peeling are likely to occur.

The support employed in the present invention is made of a synthetic fiber, and is not restricted in particular as long as the bending resistance and probe tack value of the patch agent itself can satisfy the above-mentioned conditions. Preferably used as its constituent material are films, woven fabrics, knitted fabrics, nonwoven fabrics, or their laminates comprising a synthetic resin such as a block copolymer resin mainly composed of polyester, polyethylene terephthalate (PET), ethylene/vinyl acetate copolymer (EVA), vinyl chloride, polyethylene, polybutadiene, styrene/butadiene, or styrene/isoprene, butadiene/styrene/methyl methacrylate copolymer resin, nylon, polyurethane, alkoxyalkyl (meth) acrylate copolymer, polyvinyl acetal, polyamide, or rayon. In particular, woven fabrics or nonwoven fabrics of polyester fiber yield a fine feeling and a favorable feel of use, whereby they are used more preferably in the patch agent of the present invention.

When a polyester woven fabric is used as the support in the patch agent of the present invention, it preferably has a weight per area of 80 to 120 g/m$^2$ and a fiber size of 30 to 75 deniers. When the weight per area and fiber size of the patch agent satisfy the conditions mentioned above, it tends to yield a patch agent whose feeling and feel of use such as feel of touch are very fine having a flexibility and a very high skin traceability.

Preferably, the support used in the patch agent of the present invention has an appropriate elasticity. Specifically, the load at the time of 50% elongation (defined by JIS L1096) under the measurement condition with a sample width of 50 mm, a sample length of 200 mm, and an elongation speed of 200 mm/min is preferably 100 to 1500 g in the longitudinal direction (longer side direction) and 200 to 3000 g in the lateral direction, more preferably 100 to 1000 g in the longitudinal direction (longer side direction) and 200 to 2500 g in the lateral direction. The 50% elongation recovery ratio (defined by JIS L1096) under the measurement condition with a sample width of 50 mm, a sample length of 200 mm, and an elongation speed of 200 mm/min is preferably 75% to 95% in the longitudinal direction (longer side direction) and 65% to 90% in the lateral direction, more preferably 80% to 95% in the longitudinal direction (longer side direction) and 70% to 90% in the lateral direction. If the load at the time of 50% elongation is less than the above-mentioned lower limit, then the supportiveness (nerve) of patch agent becomes insufficient, whereby the handling characteristic in attaching operations tends to deteriorate. If the load at the time of 50% elongation exceeds the above-mentioned upper limit, on the other hand, then the skin adhesiveness becomes insufficient, whereby the patch agent tends to be insufficiently prevented from peeling when applied to a bending part for a long period of time. If the 50% elongation recovery ratio is less than the above-mentioned lower limit, then the skin traceability becomes insufficient when the patch agent is applied to a bending part, whereby the patch agent tends to be insufficiently prevented from peeling. If the 50% elongation recovery ratio exceeds the above-mentioned upper limit, on the other hand, then the handling characteristic at the time of attaching operations tends to deteriorate.

Preferably, the support used in the patch agent of the present invention has a thickness of 0.01 to 5 mm. If the thickness of support is less than the above-mentioned lower limit, then the handling characteristic in attaching operations deteriorates, so that the patch agent tends to get entangled or wrinkled and becomes harder to apply finely. If the thickness of support exceeds the above-mentioned upper limit, on the other hand, then the softness of patch agent becomes insufficient, so that there is a tendency that, at the time of application, a sense of incompatibility such as twitch is felt, and physical irritations are likely to be provided.

When the patch agent of the present invention is employed as a plaster agent, an adhesive layer mainly composed of a pressure-sensitive adhesive is mounted on the above-mentioned support. Here, though the material constituting the adhesive layer is not restricted in particular as long as the bending resistance and probe tack value of the patch agent itself can satisfy the above-mentioned conditions, one which can fix a medicine onto a skin surface for a long time at room temperature is preferably used. Specific examples of such a material include acrylic adhesives, rubber adhesives, silicone adhesives, and the like. Among them, using rubber adhesives is more preferred since the physical properties of adhesive and the releasability of medicine are favorable. In particular, natural rubber, synthetic isoprene rubber, polyisobutylene rubber, polyvinyl ether, polyurethane, polyisoprene, polybutadiene, styrene/butadiene copolymer, styrene/isoprene copolymer, and styrene/isoprene/styrene block (SIS) copolymer are more preferably used. Further, when SIS copolymer is used, SIS bases manufactured by Shell Chemicals Ltd. (under the trade names of Califlex TR-1107, Califlex TR-1111, Califlex TR-1112, and Califlex TR-1117), SIS bases manufactured by Japan Synthetic Rubber Co., Ltd. (under the trade names of JSR5000, JSR5002, and JSR5100), and an SIS base manufactured by Nippon Xeon Co., Ltd. (under the trade name of Quintac 3570C) are used most preferably.

When necessary, compounding agents such as tackifiers, softeners, fillers, age resistors, and absorption accelerators may be added to the adhesive layer used in the present invention. Examples of such compounding agents include tackifiers such as alicyclic saturated hydrocarbon resins (manufactured by Arakawa Chemical Industries, Ltd. under the trade names of Alcon P-100 and the like), hydrogenated rosin esters (manufactured by Arakawa Chemical Industries, Ltd. under the trande names of KE-311 and KE-100, and manufactured by Hercules Incorporated under the trade names of Foral 105, Foral 85, and the like), hydrogenated alicyclic hydrocarbons (manufactured by Exxon Chemical Co. under the trade names of Escorez 5300 and the like), polyterpene resins, petroleum resins, and phenol resins; softeners such as liquid paraffin, polybutene, liquid polyisobutyrene, and animal and vegetable oils; other fillers; age resistors; and the like. Also, when necessary, absorption accelerators may be added to the above-mentioned pressure-sensitive adhesive in order to improve the skin permeability of medicine. Examples of such absorption accelerators include isopropyl myristate, diethyl sebacate, sorbitan monolaurate, sodium oleylphosphate, sodium laurylsulfate, octylphenyl ethers, lauryl ethers, sorbitan monolaurate, lauroyl diethanolamide, lauroyl sarcosine, oleoyl sarcosine sugar esters, lecithin, glycyrrhizin, urea, salicylic acid, calcium thioglycolate, lactic acid, lactic acid esters, olive oil, squalene, lanolin, liquid paraffin, glycerin, and the like. Further, when necessary, pigments, flavors, UV-absorbents, surfactants, pH-adjusters, and the like may appropriately be compounded in the above-mentioned pressure-sensitive adhesive.

When the patch agent of the present invention is employed in a poultice agent, an adhesive layer mainly composed of a moisture-containing ointment is mounted on the above-mentioned support. Here, though the material constituting the moisture-containing ointment is not restricted in particular as long as the bending resistance and probe tack value of the patch agent itself can satisfy the above-mentioned conditions, one which can fix amedicine onto a skin surface for a long time at room temperature is preferable. Water, thickeners, wetting agents, and fillers, and, when necessary, cross linking agents, polymerizers, solubilizers, absorption accelerators, efficacy adjuvants, stabilizers, antioxidants, emulsifiers, effective agents, and the like are added.

As the thickeners used in the moisture-containing ointment in accordance with the present invention, those which can stably hold a moisture of 30% to 80% and have a water retention are preferable. Preferably employable as specific examples thereof are water-soluble polymers such as natural polymers including those of vegetable type such as guar gum, locust bean gum, carrageenan, alginic acid, sodium alginate, agar, gum arabic, tragacanth gum, karaya gum, pectin, and starch, microorganic type such as xanthan gum and acacia gum, and animal type such as gelatin and collagen; semi-synthetic polymers including those of cellulose type such as methyl cellulose, ethyl cellulose, hydroxyethyl cellulose, and sodium carboxymethyl cellulose, and starch type such as soluble starch, carboxymethyl starch, and dialdehyde starch; and synthetic polymers including those of vinyl type such as polyvinyl alcohol, polyvinyl pyrrolidone, and polyvinyl methacrylate, acrylic type such as polyacrylic acid and sodium polyacrylate, and other synthetic polymers such as polyethylene oxide and methyl vinyl ether/maleic anhydride copolymer.

In particular, as such a thickener, polyacrylic acid is preferable in that it has a high gel strength and is excellent in water retention, and sodium polyacrylate having an average degree of polymerization of 20000 to 70000 is more preferable. As the average degree of polymerization becomes lower than 20000, the thickening effect tends to decrease, so that a sufficient gel strength may not be obtained. As the average degree of polymerization becomes higher than 70000, on the other hand, the thickening effect tends to become so strong that the operability may lower.

Examples of wetting agents employed in the moisture-containing ointment include polyhydric alcohols such as glycerin, propylene glycol, and sorbital; examples of fillers include kaolin, zinc oxide, talc, bentonite, aluminum silicate, titanium oxide, aluminum metasilicate, calcium sulfate, and calcium phosphate.

Also, propylene carbonate, crotamiton, L-menthol, mentha oil, limonene, diisopropyl adipate, and the like as a solubilizer or absorption accelerator; and methyl salicylate, glycol salicylate, L-menthol, thymol, mentha oil, limonene, nonylic acid vanillylamide, pepper extract, and the like as an efficacy adjuvant may be added to the moisture-containing ointment in accordance with the present invention. Further, when necessary, stabilizers, antioxidants, emulsifiers, and the like may be added to the moisture-containing ointment in accordance with the present invention.

Further, when necessary, crosslinking agents, polymerizers, and the like may be added to the moisture-containing ointment so as to strengthen the moisture-containing ointment (adhesive) and cause it to yield water retention. Such crosslinking agents and polymerizers can appropriately be chosen according to the kind of thickeners and the like.

For example, in the case where polyacrylic acid or polyacrylate is employed as a thickener, compounds having at least two pieces of epoxy group in a molecule; inorganic acid salts such as hydrochlorides, sulfates, phosphates, and carbonates of Ca, Mg, Al, and the like; organic acid salts such as citrates, tartrates, gluconates, and stearates; oxides such as zinc oxide and silicic anhydride; and polyvalent metal compounds such as hydroxides like aluminum hydroxide and magnesium hydroxide are preferably used. In the case where polyvinyl alcohol is employed as a thickener, adipic acid, thioglycolic acid, epoxy compounds (epichlorohydrin), aldehydes, N-methylol compounds, and complexes of Al, Ti, Zr, Sn, V, Cu, B, and Cr are preferably used. When polypyrrolidone is employed as a thickener, methyl vinyl ester/maleic anhydride copolymer, polyacid compounds, or alkali metal salts (polyacrylic acid, tannic acid, and their derivatives) are preferably used. When polyethylene oxide is employed as a thickener, peroxide or polysulfone azide is preferably used. When methyl vinyl ether/maleic anhydride copolymer is employed as a thickener, polyfunctional hydroxyl compounds, polyamines, iodine, gelatin, polyvinyl pyrrolidone, iron, mercury, and lead salts are preferably used. When gelatin is employed as a thickener, aldehydes such as formaldehyde, glutaraldehyde, dialdehyde starch; diepoxides such as glyoxal and butadiene oxide; diketones such as divinyl ketone; and diisocyanates are preferably used.

When thus configured plaster agent, poultice agent, or the like is caused to hold a medicine, it will be sufficient if the medicine is compounded in the adhesive layer thereof. Examples of the medicine used in the patch agent of the present invention include general anesthetics, hypnotic analgesics, antipyretic/antiphlogistic analgesics, steroid hormone drugs, analeptics/stimulants, psychiatric/neurological drugs, local anesthetics, skeletal muscle relaxants, drugs for autonomic nerves, antiallergic agents, antihistamine agents, cardiotonics, drugs for arrhythmia, diuretics, hypotensive agents, vasoconstrictors, vasodilators, calcium antagonists, antibacterial/bactericidal agents, drugs for parasitic dermatosis, skin softeners, antibiotics, antidotes, cough remedies, antipruritics, sleeping drugs, psychiatric activators, drugs for asthma, hormone secretion accelerators, antiulcer agents, anticancer drugs, vitamin compounds, and those having a whitening effect such as skin care components.

The thickness (coating thickness) of the adhesive layer mounted on the support in the patch agent of the present invention is preferably 0.05 to 3 mm. If the thickness of adhesive layer exceeds 3 mm, then the releasability of the medicine contained in the adhesive layer tends to lower. If it is less than 0.05 mm, on the other hand, then the skin adhesiveness tends to lower, so that the peel-off may not fully be prevented from occurring.

Preferably, the thickness including the support and the thickening agent in the patch agent of the present invention (the thickness of patch agent) is 0.3 to 5 mm. If the thickness of patch agent exceeds 5 mm, then edges of the patch agent tend to catch on cloths and the like at the time of application, thereby peeling off. If the thickness of patch agent is less than 0.3 mm, on the other hand, then the supportiveness of patch agent tends to lower, thereby generating such phenomena as failing to securely attach to a part to be applied, entangling, and wrinkling after application.

Preferably, corners in the patch agent of the present invention are cut in arc forms. Once a poultice agent partly turns over and peels off, horny layers of skin and dust attach to this part, which makes it difficult for the poultice agent to be applied again. When the patch agent has a rectangular form in particular, corners tend to catch on cloths and the like and turn over at first, thereby peeling off. Therefore, it is preferred that corners of the patch agent be formed like an arc, so as to be unlikely to catch on cloths and the like, whereby the peel-off tends to be more effectively prevented from occurring.

When corners in the poultice agent of the present invention are formed like an arc, it is preferred that the arc have a radius of curvature (R) of 5 to 20 mm. If the radius (R) is less than 5 mm, then the reduction in peel-off at the time of application tends to be achieved insufficiently. If it exceeds 20 mm, on the other hand, then the phenomenon of peeling off from corners is prevented from occurring, but the loss at the time of manufacture tends to be so large that the manufacturing cost increases, which is poor in actual profit.

In the patch agent of the present invention, it is preferred that a release sheet having an appropriate bending resistance be attached to a surface of the adhesive layer thereof. Specifically, it is preferred that a release sheet having a bending resistance of 60 to 160 mm beat tached thereto. Attaching such a release sheet to the patch agent improves the supportiveness of patch agent, whereby the patch agent tends to be applied finely and securely without generating entanglement, wrinkles, and the like. If the bending resistance of release sheet is less than 60 mm, then the supportiveness tends to become insufficient, so that the patch agent may twist and get entangled or wrinkle after being applied. If the bending resistance of release sheet exceeds 160 mm, on the other hand, then the release sheet becomes harder, whereby the operability at the time of peeling off the release sheet from the poultice agent tends to lower.

The material for such a release sheet is not restricted in particular as long as the bending resistance of release sheet satisfies the condition mentioned above. Specifically, plastic films such as cast polypropylene (CPP), oriented polypropylene (OPP), polyethylene terephthalate (PET), polybutylene terephthalate (PBT), polyethylene, polyester, polyurethane, polyvinyl chloride, and polystyrene, silicone-treated paper such as silicone-treated synthetic resin, synthetic paper, and synthetic fiber, aluminum foil, and laminate-processed paper in which polyethylene or the like is laminated on kraft paper, which are left uncolored or colored, are preferably used. Among them, polyethylene terephthalate (PET) is preferably used in particular.

The thickness of the release sheet used in the patch agent of the present invention is preferably 10 to 100 $\mu$m, more preferably 30 to 90 $\mu$m, further preferably 40 to 85 $\mu$m. If the release sheet has a thickness of less than 10 $\mu$m, then it is harder to hold and more likely to get entangled with the adhesive layer when peeling off the release sheet. On the other hand, though the release sheet becomes easier to hold as its thickness increases, if it exceeds 100 $\mu$m, then it becomes difficult to cut the raw material sheet, whereby the operability (manufacturing efficiency) tends to lower.

The release sheet used in the patch agent of the present invention preferably has a continuous or intermittent cutting portion at a predetermined part such as a substantially center part thereof. Using are lease sheet having a cutting portion tends to be effective in not only improving the feel of use in that it can be applied finely and securely without soiling hands, but also improving the working efficiency in that an operation for peeling off the release sheet and an operation for applying the patch agent can be carried out at the same time.

Figure 2:
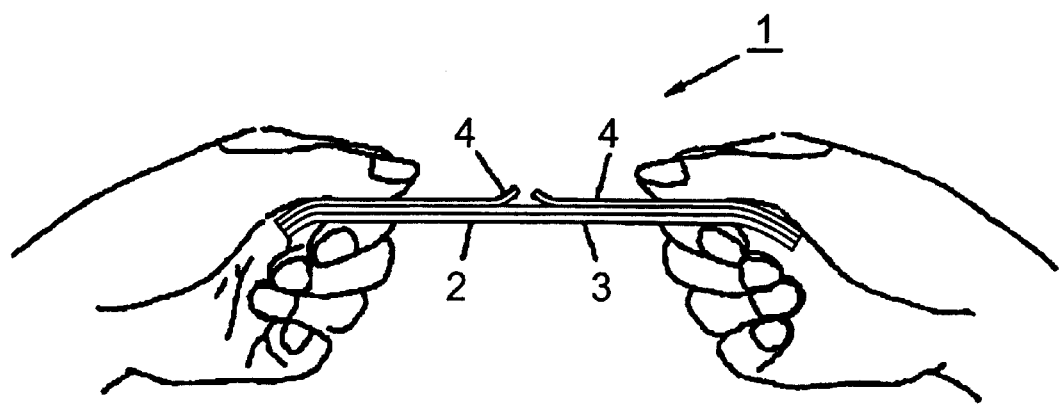
FIG. 2 is an explanatory view showing an example of the method of using the patch agent of the present invention.
Figure 3:
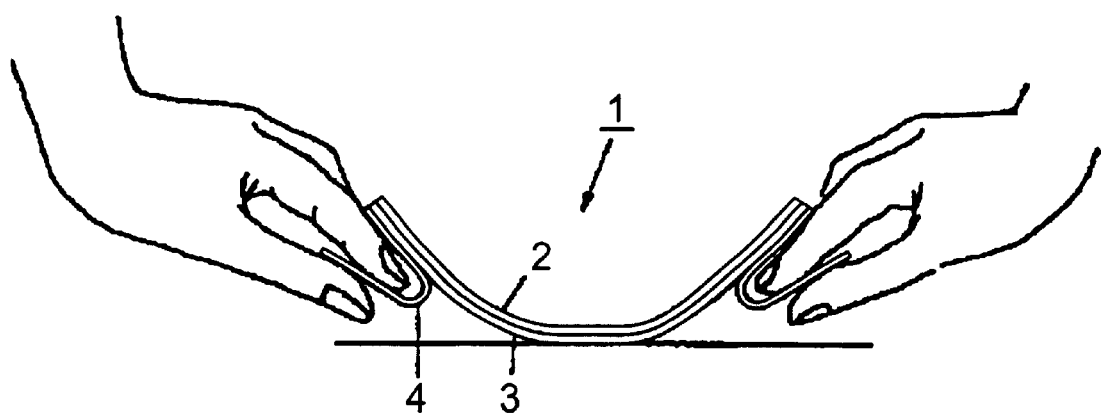
FIG. 3 is an explanatory view showing an example of the method of using the patch agent of the present invention.

Namely, when the patch agent of the present invention comprises a release sheet having a cutting portion, it can be used in conformity with the method of use explained in the following. FIG. 2 is an explanatory view showing an operation for severing the release sheet 4 of patch agent 1, whereas FIG. 3 is an explanatory view showing an operation for attaching the patch agent 1 to a part to be applied. First, as shown in FIG. 2, both ends of the patch agent 1 are picked, the release sheet 4 is pulled together with the support 2, and the cutting portion is slightly bent, whereby the release sheet 4 can laterally be severed along the cutting portion. When apart of the cutting portion is just slightly bent, the severed release sheet 4 turns up from the severed portion due to the elasticity of release sheet, thus exposing the adhesive layer 3. Then, as shown in FIG. 3, while thus exposed adhesive layer is brought into contact with an affected part, the individual turned-up parts are pulled left ward and right ward, respectively, and peeled off, whereby the operation for peeling off the release sheet 4 and the operation for attaching the patch agent 1 to the affected part are carried out at the same time. Thus, using the patch agent comprising a release sheet having a cutting portion tends to improve the feel of use and operating efficiency of the patch agent.

EXAMPLES

In the following, the present invention will be explained more specifically with reference to Examples and Comparative Examples, though the present invention will not be restricted to the following examples at all.

Example 1

Into a mixer, 70 parts by weight of purified water, 3 parts by weight of gelatin, 2 parts by weight of polyvinyl alcohol, and 2 parts by weight of kaolin were introduced; and they were mixed at a temperature of about 50° C., whereby a uniform dispersion was obtained. Then, a dispersion prepared beforehand comprising 13 parts by weight of glycerin, 5 parts by weight of sodium polyacrylate, 2 parts by weight of methyl vinyl ether/maleic anhydride copolymer, and 1 part by weight of aluminum hydroxide were added to the former dispersion, and stirred and mixed therewith. Further, a solution in which 0.5 part by weight of ketoprofen was dissolved into 1.5 parts by weight of mentha oil was added thereto and stirred and mixed together, whereby a uniform mixture was obtained.

Subsequently, thus obtained mixture was spread over a polypropylene film (having a bending resistance of 75 mm) such that the weight after drying became 10 g/140 cm$^2$, and then covered with a support made of polyester woven fabric (having a fiber size of 75 deniers and a weight per area of 120 g/m$^2$) so as to be transferred thereto under pressure. Thus obtained product was cut, such that the aimed patch agent was obtained as a poultice agent having a length of 10 cm, a width of 14 cm, and a thickness of 2.00 mm.

Example 2

Into a mixer, 31.92 parts by weight of purified water, 3 parts by weight of gelatin, 3 parts by weight of polyvinyl pyrrolidone, and 3 parts by weight of zinc oxide were introduced; and they were mixed at a temperature of about 50° C., whereby a uniform dispersion was obtained. Then, a dispersion prepared beforehand comprising 50 parts by weight of polyethylene glycol, 4 parts by weight of sodium polyacrylate, 3 parts by weight of polyacrylic acid, and 0.08 parts by weight of polyethylene glycol diglycidyl ether were added to the former dispersion, and stirred and mixed therewith. Further, a solution in which 0.5 part by weight of suprofen was dissolved into 1.5 parts by weight of benzyl alcohol was added thereto and stirred and mixed therewith, whereby a uniform mixture was obtained.

Subsequently, thus obtained mixture was spread over a polyethylene film (having a bending resistance of 130 mm) such that the weight after drying became 5 g/140 cm$^2$, and then covered with polypropylene woven fabric (having a fiber size of 35 deniers and a weight per area of 110 g/m$^2$) so as to be transferred thereto under pressure. Thus obtained product was cut, such that the aimed patch agent was obtained as a poultice agent having a length of 10 cm, a width of 14 cm, and a thickness of 2.00 mm.

Example 3

Into 78.4 parts by weight of purified water, 4 parts by weight of synthetic aluminum silicate was dispersed. Then, 1 part by weight of gelatin, 0.05 part by weight of sorbitol polyglycidyl ether, 0.2 part by weight of water-soluble placenta extract, 0.1 part by weight of allantoin, and 0.25 part by weight of methyl paraben were added thereto and mixed together. Further, 6 parts by weight of sodium polyacrylate and 10 parts by weight of polyethylene glycol were added thereto and stirred together, whereby a uniform mixture was obtained.

Subsequently, thus obtained mixture was spread over a polyester film (having a bending resistance of 120 mm) such that the weight after drying became 10 g/140 cm$^2$, and then covered with polyester woven fabric (having a fiber size of 60 deniers and a weight per area of 110 g/m$^2$) so as to be transferred thereto under pressure. Thus obtained product was cut, such that the aimed patch agent was obtained as a sheet-like pack agent having a length of 10 cm, a width of 14 cm, and a thickness of 2.00 mm.

Example 4

In a nitrogen gas atmosphere, 26 parts by weight of styrene/isoprene/styrene block copolymer (Krayton D-1107CU manufactured by Shell Chemicals), 22 parts by weight of polyisobutylene (Opanol B80 manufactured by BASF), 10 parts by weight of hydrogenated rosin ester (Stebelite Ester 7 manufactured by Rika-Hercules), 38 parts by weight of liquid paraffin (Crystol J-352 manufactured by Esso Oil), and 1 part by weight of dibutyl hydroxytoluene were heated and stirred for 60 minutes at 200° C., whereby a solution was obtained. To this solution, 3 parts by weight of ketoprofen were added at 150° C. (110 to 200° C.); and they were mixed for 15 minutes, whereby a uniform mixture was obtained.

Subsequently, thus obtained mixture was spread over a silicone-treated polyester film (having a bending resistance of 65 mm) such that the weight after drying became 1 g/70 cm$^2$, and then covered with polyester woven fabric (having a fiber size of 50 deniers and a weight per area of 80 g/m$^2$) so as to be transferred thereto under pressure. Thus obtained product was cut, such that the aimed patch agent was obtained as a tape agent having a length of 7 cm, a width of 10 cm, and a thickness of 0.60 mm.

Example 5

In a nitrogen gas atmosphere, 23 parts by weight of styrene/isoprene/styrene block copolymer (Krayton D-KX401CS manufactured by Shell Chemicals), 22 parts by weight of polyisobutylene (Vistanex MML-80 manufactured by Exxon Chemical), 23 parts by weight of petroleum resin (Escorez 5300 manufactured by Exxon Chemical), 24 parts by weight of liquid paraffin (Crystol J-352 manufactured by Esso Oil), and 3 parts by weight of titanium oxide were heated and stirred for 60 minutes at 200° C., whereby a solution was obtained. To this solution, 5 parts by weight of diclofenac sodium were added at 150° C; and they were mixed for 15 minutes, whereby a uniform solution was obtained.

Subsequently, thus obtained solution was spread over a silicone-treated polyester film (having a bending resistance of 160 mm) such that the weight after drying became 1 g/70 cm², and then covered with polyester woven fabric (having a fiber size of 30 deniers and a weight per area of 120 g/m²) so as to be transferred thereto under pressure. Thus obtained product was cut, such that the aimed patch agent was obtained as a tape agent having a length of 7 cm, a width of 10 cm, and a thickness of 0.75 mm.

Example 6

In a nitrogen gas atmosphere, 16 parts by weight of styrene/isoprene/styrene block copolymer (Krayton D-KX401CS manufactured by Shell Chemicals), 10 parts by weight of polyisobutylene (Vistanex MML-100 manufactured by Exxon Chemical), 25 parts by weight of hydrogenated rosin glycerin ester (manufactured by Arakawa Chemical Industries), 36 parts by weight of liquid paraffin (Crystol J-352 manufactured by Esso Oil), and 3 parts by weight of synthetic aluminum silicate were heated and stirred for 60 minutes at 200° C., and then 5 parts by weight of methyl salicylate and 5 parts by weight of L-menthol were further added thereto at 150° C. and mixed for 15 minutes, whereby a uniform mixture was obtained.

Subsequently, thus obtained mixture was spread over a silicone-treated polyester film (having a bending resistance of 160 mm) such that the weight after drying became 1 g/70 cm², and then covered with polyester woven fabric (having a fiber size of 75 deniers and a weight per area of 80 g/m²) so as to be transferred thereto under pressure. Thus obtained product was cut, such that the aimed patch agent was obtained as a tape agent having a length of 7 cm, a width of 10 cm, and a thickness of 0.55 mm.

Comparative Example 1

Into a reactor, 55 parts by weight of acrylic acid 2-ethylhexyl ester, 26 parts by weight of acrylic acid methoxyethyl ester, 14.7 parts by weight of vinyl acetate, 0.3 part by weight of azobisisobutyronitrile, and 100 parts by weight of ethyl acetate were introduced. Subsequently, they were heated to 60° C. in a nitrogen atmosphere so as to initiate polymerization, the reaction was carried out for 10 hours, and then the mixture was further matured for 2 hours at 60° C., whereby a copolymer solution was obtained. To thus obtained copolymer solution, 4 parts by weight of ketoprofen were added; and they were mixed together, whereby a uniform mixture solution was obtained.

Thus obtained mixture was spread over a silicone-treated polyester film (having a bending resistance of 120 mm) such that the weight after drying became 0.5 g/70 cm², and then covered with polyester woven fabric (having a fiber size of 35 deniers and a weight per area of 90 g/m²) so as to be transferred thereto under pressure. Thus obtained product was cut, such that the aimed patch agent was obtained as a tape agent having a length of 7 cm, a width of 10 cm, and a thickness of 0.45 mm.

Comparative Example 2

Into a reactor, 47.47 parts by weight of purified water, 1 part by weight of agar, 2 parts by weight of polyvinyl alcohol, and 2 parts by weight of titanium oxide were introduced; and they were dissolved at a temperature of about 50° C., whereby a uniform dispersion was obtained. Subsequently, a dispersion prepared beforehand comprising 26 parts by weight of glycerin, 15 parts by weight of sorbitol, 5.7 parts by weight of sodium polyacrylate, and 0.03 part by weight of polyglycerol polyglycidyl ether was added thereto, and stirred and mixed therewith. Further, a solution in which 0.3 part by weight of crotamiton and 0.5 part by weight of piroxi cam were dissoluted was added thereto, and stirred and mixed therewith, whereby a uniform mixture was obtained.

Thus obtained mixture was spread over a polyethylene film (having a bending resistance of 40 mm) such that the weight after drying became 5 g/140 cm², and then covered with a support made of polyester woven fabric (having a fiber size of 35 deniers and a weight per area of 60 g/m²) so as to be transferred thereto under pressure. Thus obtained product was cut, such that the aimed patch agent was obtained as a poultice agent having a length of 10 cm, a width of 14 cm, and a thickness of 0.80 mm.

Comparative Example 3

In a nitrogen gas atmosphere, 26 parts by weight of styrene/isoprene/styrene block copolymer (Krayton D-1107CU manufactured by Shell Chemicals), 8 parts by weight of hydrogenated rosin glycerin ester (manufactured by Arakawa Chemical Industries), 55 parts by weight of liquid paraffin (Crystol J-352 manufactured by Esso Oil), and 3 parts by weight of synthetic aluminum silicate were heated and stirred for 60 minutes at 200° C., and then 3 parts by weight of ketoprofen and 5 parts by weight of L-menthol were further added thereto at 150° C. and mixed for 15 minutes, whereby a uniform mixture was obtained.

Subsequently, thus obtained mixture was spread over a silicone-treated polyester film (having a bending resistance of 180 mm) such that the weight after drying became 1 g/70 cm², and then covered with a support made of polyester woven fabric (having a fiber size of 25 deniers and a weight per area of 60 g/m²) so as to be transferred thereto under pressure. Thus obtained product was cut, such that the aimed patch agent was obtained as a tape agent having a length of 7 cm, a width of 10 cm, and a thickness of 0.50 mm.

Comparative Example 4

In a nitrogen gas atmosphere, 17 parts by weight of styrene/isoprene/styrene block copolymer (SIS-5000 manufactured by Japan Synthetic Rubber), 52 parts by weight of hydrogenated rosin glycerin ester (manufactured by Arakawa Chemical Industries), and 21 parts by weight of liquid paraffin (Crystol J-352 manufactured by Esso Oil) were heated and stirred for 60 minutes at 200° C., whereby a solution was obtained. To this solution, 5 parts by weight of glycol salicylate and 5 parts by weight of L-menthol were further added at 150° C. and mixed for 15 minutes, whereby a uniform mixture was obtained.

Subsequently, thus obtained mixture was spread over a silicone-treated polyester film (having a bending resistance of 100 mm) such that the weight after drying became 1 g/70 cm², and then covered with a support made of polyvinyl chloride film (having a weight per area of 110 g/m²) so as to be transferred thereto under pressure. Thus obtained product was cut, such that the aimed patch agent was obtained as a tape agent having a length of 7 cm, a width of 10 cm, and a thickness of 0.25 mm.

Table 1 shows the bending resistance and probe tack value of each of thus obtained patch agents.

TABLE 1

|  | BENDING RESISTANCE (mm) | PROBE TACK VALUE (N) |
|---|---|---|
| EXAMPLE 1 | 22 | 0.44 |
| EXAMPLE 2 | 18 | 0.73 |
| EXAMPLE 3 | 30 | 0.25 |
| EXAMPLE 4 | 10 | 0.83 |
| EXAMPLE 5 | 20 | 1.10 |
| EXAMPLE 6 | 15 | 0.78 |

TABLE 1-continued

|  | BENDING RESISTANCE (mm) | PROBE TACK VALUE (N) |
|---|---|---|
| COMP. EX. 1 | 14 | 1.76 |
| COMP. EX. 2 | 7 | 0.20 |
| COMP. EX. 3 | 12 | 0.15 |
| COMP. EX. 4 | 40 | 2.75 |

Next, the following evaluation tests were carried out while using the individual patch agents of Examples 1 to 6 and Comparative Examples 1 to 4.

Sensory Application Test

Concerning the feel of use of each of the patch agents of Examples 1 to 6 and Comparative Examples 1 to 4, a sensory attachment test was carried out for 30 normal adult males. Namely, the testers applied the individual patch agents to elbows on different days, performed an operation of peeling them off after 6 hours of application, and evaluated three evaluation items of "easiness to apply at the time of applying operation," "resistance to peel at the time of application," and "pain at the time of peel-off" according to their corresponding criteria shown in Table 2. Thus obtained results are shown in Table 2. The evaluations in Table 2 are classified according to the number of items in which the number of testers who did the worst evaluations of "hard to apply," "¼ or more peeled off," and "pain" was 5 or more, such that rank A refers to the case where the number of items corresponding thereto among the above-mentioned three items was 0, rank B refers to the case where the number was 1, and rank C refers to the case where the number was 2 or greater.

TABLE 2

|  | EASINESS TO APPLY | | | RESISTANCE TO PEEL | | |
|---|---|---|---|---|---|---|
|  | HARD TO APPLY (PERSON) | NEITHER HARD NOR EASY (PERSON) | EASY TO APPLY (PERSON) | NO PEEL-OFF (PERSON) | EDGE PORTION PEELED (PERSON) | ¼ OR MORE PEELED (PERSON) |
| EXAMPLE 1 | 1 | 4 | 25 | 23 | 5 | 2 |
| EXAMPLE 2 | 2 | 6 | 22 | 25 | 4 | 1 |
| EXAMPLE 3 | 0 | 5 | 25 | 22 | 6 | 2 |
| EXAMPLE 4 | 4 | 5 | 21 | 25 | 5 | 0 |
| EXAMPLE 5 | 0 | 4 | 26 | 27 | 2 | 1 |
| EXAMPLE 6 | 3 | 5 | 22 | 26 | 4 | 0 |
| COMP. EX. 1 | 5 | 6 | 19 | 28 | 2 | 0 |
| COMP. EX. 2 | 18 | 12 | 0 | 10 | 8 | 12 |
| COMP. EX. 3 | 24 | 6 | 0 | 5 | 8 | 7 |
| COMP. EX. 4 | 5 | 12 | 13 | 27 | 2 | 1 |

|  | PAIN UPON PEELING | | | |
|---|---|---|---|---|
|  | NO PAIN (PERSON) | SLIGHT PAIN (PERSON) | PAIN (PERSON) | EVALUATION |
| EXAMPLE 1 | 28 | 2 | 0 | A |
| EXAMPLE 2 | 24 | 6 | 0 | A |
| EXAMPLE 3 | 29 | 1 | 0 | A |
| EXAMPLE 4 | 26 | 4 | 0 | A |
| EXAMPLE 5 | 24 | 4 | 2 | A |
| EXAMPLE 6 | 23 | 6 | 1 | A |
| COMP. EX. 1 | 0 | 3 | 27 | C |
| COMP. EX. 2 | 30 | 0 | 0 | C |
| COMP. EX. 3 | 26 | 4 | 0 | C |
| COMP. EX. 4 | 2 | 4 | 24 | C |

Skin Safety Test (Normal Subject Patch Test)

In the above-mentioned sensory application test, the state of skin at the part of application after peeling off each patch agent is evaluated according to the following criteria:
  −: no reaction;
  ±: erythema is slightly seen;
  +: erythema is clearly seen;
  ++: erythema, and papule or edema are seen; and
  +++: erythema, papule or edema, and vesicle are seen.

Thus obtained results are shown in Table 3. The evaluations in Table 3 are classified such that rank A refers to the case where the ratio of occurrence of ± to +++ in the above-mentioned criteria is 10% or less, rank B refers to the case where the ratio is more than 10% but not exceeding 25%, and rank C refers to the case where the ratio exceeds 25%.

TABLE 3

| | EVALUATION | | | | | | |
|---|---|---|---|---|---|---|---|
| | +++ (PERSON) | ++ (PERSON) | + (PERSON) | ± (PERSON) | − (PERSON) | TOTAL (PERSON) | EVALUATION |
| EXAMPLE 1 | 0 | 0 | 0 | 1 | 29 | 30 | A |
| EXAMPLE 2 | 0 | 0 | 0 | 2 | 28 | 30 | A |
| EXAMPLE 3 | 0 | 0 | 0 | 0 | 30 | 30 | A |
| EXAMPLE 4 | 0 | 0 | 0 | 3 | 27 | 30 | A |
| EXAMPLE 5 | 0 | 0 | 0 | 2 | 28 | 30 | A |
| EXAMPLE 6 | 0 | 0 | 0 | 2 | 28 | 30 | A |
| COMP. EX. 1 | 0 | 0 | 0 | 11 | 19 | 30 | C |
| COMP. EX. 2 | 0 | 0 | 0 | 2 | 28 | 30 | A |
| COMP. EX. 3 | 0 | 0 | 0 | 3 | 27 | 30 | A |
| COMP. EX. 4 | 0 | 0 | 0 | 10 | 20 | 30 | C |

Table 4 shows the total evaluation according to the results of sensory application test and skin safety test mentioned above. The criteria for the total evaluation in Table 4 are as follows:

A: both of the above-mentioned tests are evaluated A;

B: one of the above-mentioned tests is A to B, whereas the other is B;

C: one of the above-mentioned tests is A to B, whereas the other is C; and

D: both of the above-mentioned tests are evaluated C.

TABLE 4

| | EVALUATION | | |
|---|---|---|---|
| | SENSORY APPLICATION TEST (FEEL OF USE) | SKIN SAFETY TEST (RESISTANCE TO RASH) | TOTAL EVALUATION |
| EXAMPLE 1 | A | A | A |
| EXAMPLE 2 | A | A | A |
| EXAMPLE 3 | A | A | A |
| EXAMPLE 4 | A | A | A |
| EXAMPLE 5 | A | A | A |
| EXAMPLE 6 | A | A | A |
| COMP. EX. 1 | C | C | D |
| COMP. EX. 2 | C | A | C |
| COMP. EX. 3 | C | A | C |
| COMP. EX. 4 | C | C | D |

As shown in Tables 2 to 4, it was verified that each of the patch agents of examples 1 to 6 was an excellent patch agent yielding favorable feel of use in all the items of the easiness to apply, resistance to peel, and pain at the time of peeling, while fully suppressing the rash of skin.

By contrast, the patch agents of Comparative Examples 1 and 4 accompanied pains at the time of peeling, though they were hard to peel off, and the ratio of occurrence of rash was high. Though the ratio of occurrence of rash was low, the patch agents of Comparative Examples 2 and 3 were insufficient in terms of the easiness to apply and resistance to peel, thereby failing to yield favorable feel of use.

INDUSTRIAL APPLICABILITY

As explained in the foregoing, the present invention yields a patch agent which is fully prevented from peeling off at the time of application and fully suppresses the rash of skin and the pain upon peeling.

What is claimed is:

1. A patch agent comprising a support made of a synthetic fiber and an adhesive layer mounted on said support, said patch agent having a bending resistance of 10 to 30 mm and a probe tack value of 0.25 to 1.2 N.

2. A patch agent according to claim 1, wherein said patch agent comprises a release sheet attached to a surface of said adhesive layer, said release sheet having a bending resistance of 60 to 160 mm.

3. A patch agent according to claim 1, wherein said support is made of a polyester fiber having a fiber size of 30 to 75 deniers, and has a weight per area of 80 to 120 g/m².

* * * * *

UNITED STATES PATENT AND TRADEMARK OFFICE
CERTIFICATE OF CORRECTION

PATENT NO. : 6,914,169 B1
DATED : July 5, 2005
INVENTOR(S) : Shigeo Oota and Kiyomi Tsuruda It is certified that error appears in the above-identified patent and that said Letters Patent is hereby corrected as shown below:

Title page,
Item [22], PCT Filed, "May 19, 2000" should be -- May 2, 2001 --.

Signed and Sealed this

Tenth Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,914,169 B1 Page 1 of 1
APPLICATION NO. : 10/276423
DATED : July 5, 2005
INVENTOR(S) : Shigeo Oota and Kiyomi Tsuruda It is certified that error appears in the above-identified patent and that said Letters Patent is hereby corrected as shown below:

<u>Title page,</u>
Item [22], PCT Filed, "May 19 2000" should be -- May 2, 2001 --.

Signed and Sealed this

Fifteenth Day of August, 2006

JON W. DUDAS
*Director of the United States Patent and Trademark Office*

(12) INTER PARTES REEXAMINATION CERTIFICATE (701st)

United States Patent
Oota et al.

(10) Number: US 6,914,169 C1
(45) Certificate Issued: Oct. 7, 2013

(54) PATCH AGENT

(75) Inventors: Shigeo Oota, Tokyo (JP); Kiyomi Tsuruda, Tosu (JP)

(73) Assignee: Hismitsu Pharmaceutical Co, Inc., Tashirodaikan-Machi, Toshu-shi, Saga A (JP)

Reexamination Request:
No. 95/001,603, Apr. 15, 2011

Reexamination Certificate for:
Patent No.: 6,914,169
Issued: Jul. 5, 2005
Appl. No.: 10/276,423
Filed: Nov. 15, 2002

Certificate of Correction issued Jan. 10, 2006
Certificate of Correction issued Aug. 15, 2006

(21) Appl. No.: 95/001,603
(22) PCT Filed: May 2, 2001
(86) PCT No.: PCT/JP01/03806
§ 371 (c)(1),
(2), (4) Date: Nov. 15, 2002
(87) PCT Pub. No.: WO01/87275
PCT Pub. Date: Nov. 22, 2001

(30) Foreign Application Priority Data

May 19, 2000 (JP) .................................. 2000-148260

(51) Int. Cl.
*A61L 15/58* (2006.01)
*A61L 15/16* (2006.01)

(52) U.S. Cl.
USPC .................... 602/58; 602/43; 602/54; 602/57

(58) Field of Classification Search
USPC ........................................................... 602/54
See application file for complete search history.

(56) References Cited

To view the complete listing of prior art documents cited during the proceeding for Reexamination Control Number 95/001,603, please refer to the USPTO's public Patent Application Information Retrieval (PAIR) system under the Display References tab.

*Primary Examiner* — Eileen Lillis

(57) ABSTRACT

The patch agent of the present invention is a patch agent comprising a support made of a synthetic fiber and an adhesive layer mounted on the support, and having a bending resistance of 10 to 30 mm and a probe tack value of 0.25 to 1.2 N. The patch agent of the present invention can fully be prevented from peeling off at the time of application and can fully suppress the rash of skin and the pain upon peeling.

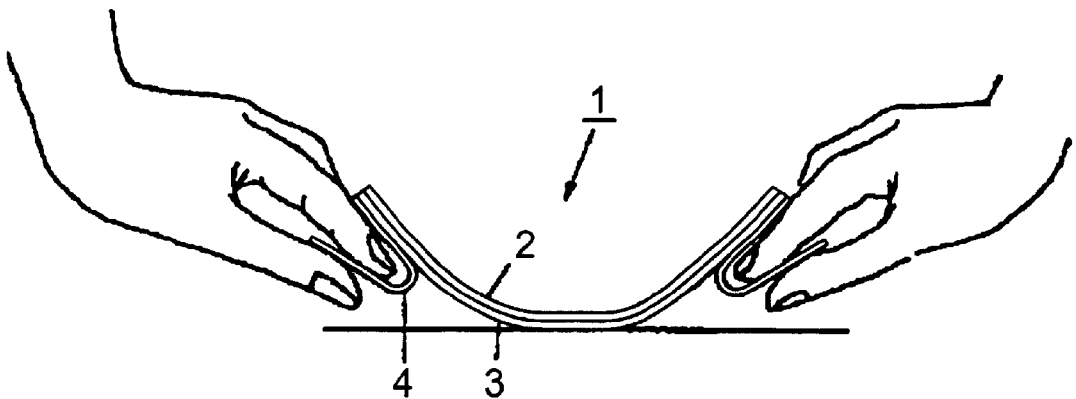

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-3 are cancelled.

\* \* \* \* \*